(12) United States Patent
D'Aquanni et al.

(10) Patent No.: US 7,643,886 B2
(45) Date of Patent: Jan. 5, 2010

(54) HYDRAULIC ACTUATION OF LEAD FIXATION MEMBER

(75) Inventors: Peter J. D'Aquanni, Murrieta, CA (US); Eric T. Johnson, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 176 days.

(21) Appl. No.: 11/627,224

(22) Filed: Jan. 25, 2007

(65) Prior Publication Data

US 2008/0183266 A1 Jul. 31, 2008

(51) Int. Cl.
*A61N 1/00* (2006.01)
(52) U.S. Cl. ..................................... 607/126
(58) Field of Classification Search .......... 607/116, 607/126; 600/373, 381
See application file for complete search history.

(56) References Cited

U.S. PATENT DOCUMENTS

| 4,884,567 | A | 12/1989 | Elliott et al. |
| 5,179,962 | A | 1/1993 | Dutcher et al. |
| 5,192,295 | A | 3/1993 | Danforth et al. |
| 5,344,439 | A * | 9/1994 | Otten .................. 607/126 |
| 5,445,646 | A | 8/1995 | Euteneuer et al. |
| 5,989,263 | A | 11/1999 | Shmulewitz |
| 6,027,474 | A | 2/2000 | Douk et al. |
| 6,428,557 | B1 | 8/2002 | Hilaire |
| 6,530,947 | B1 | 3/2003 | Euteneuer et al. |
| 2002/0045929 | A1 | 4/2002 | Diaz |
| 2003/0114844 | A1 | 6/2003 | Ormsby et al. |
| 2003/0114879 | A1 | 6/2003 | Euteneuer et al. |
| 2005/0288700 | A1 | 12/2005 | Chermoni |

OTHER PUBLICATIONS

International Search Report and Written Opinion of international application No. PCT/US2008/051698, mailed Jun. 18, 2008, 14 pp.

* cited by examiner

*Primary Examiner*—George Manuel
*Assistant Examiner*—Shubatra Narayanaswamy
(74) *Attorney, Agent, or Firm*—Faegre & Benson LLP

(57) ABSTRACT

A medical electrical lead includes a primary lumen, a hydraulic lumen, and a fixation portion including at least one expandable fixation member. The fixation member communicates with a plunger disposed in the hydraulic lumen, and is actuated from an expanded configuration to a collapsed configuration by the introduction and release of hydraulic pressure in the hydraulic lumen. The hydraulic actuation of the fixation member allows for the delivery, positioning, re-positioning, and/or retrieval of the lead.

20 Claims, 16 Drawing Sheets

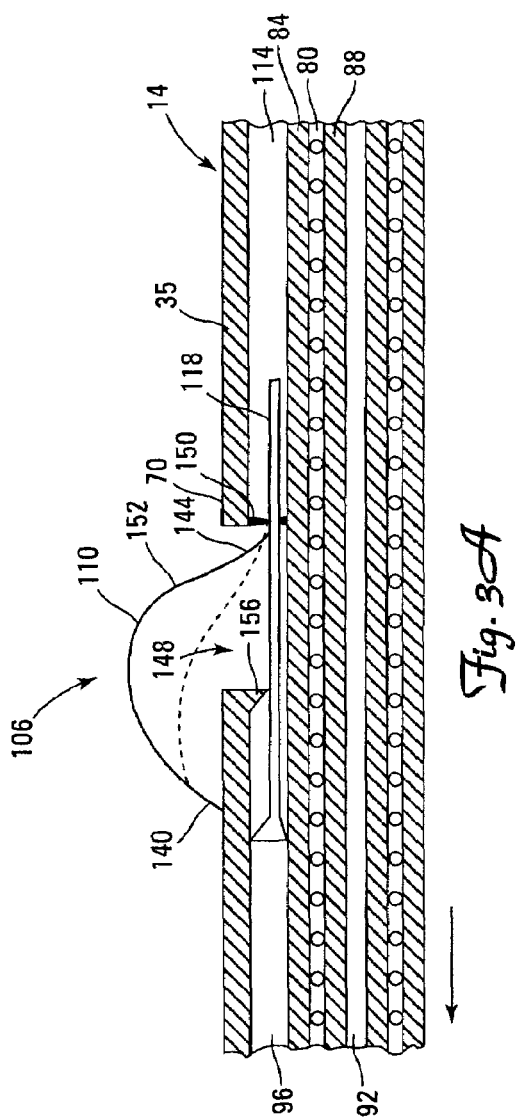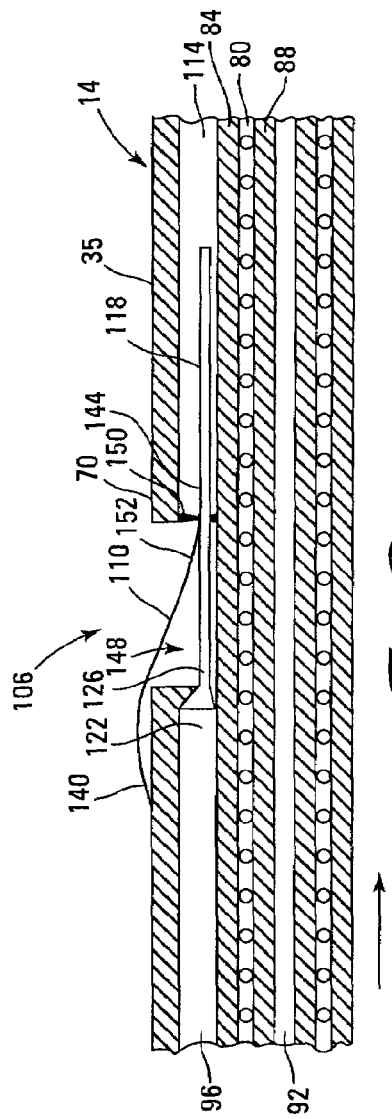

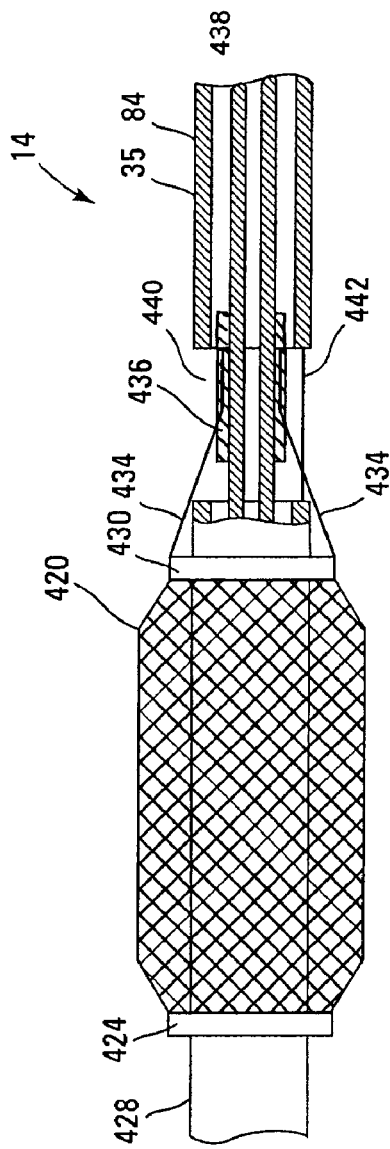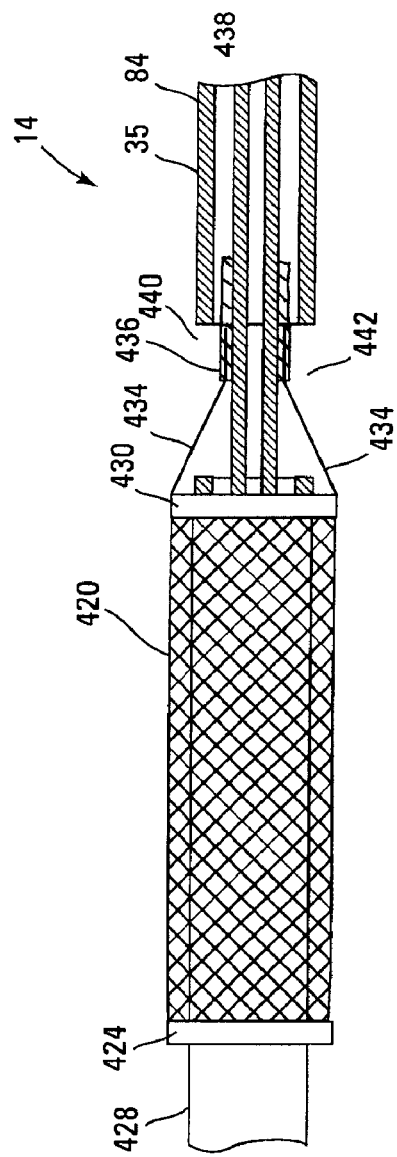
Fig. 10A
Fig. 10B

HYDRAULIC ACTUATION OF LEAD FIXATION MEMBER

TECHNICAL FIELD

The present invention relates to devices and methods for fixation of medical electrical leads. Specifically, the present invention is directed to deployable devices and methods for acute and chronic fixation of a portion of a medical electrical lead within a patient's vasculature, and in particular, the coronary vasculature.

BACKGROUND

Implantable medical devices for treating irregular contractions of the heart with electrical stimuli are known. Exemplary implantable devices are defibrillators and pacemakers. Various types of electrical leads for defibrillators and pacemakers have been suggested, many of which are placed transvenously. Such leads are introduced into the patient's vasculature at a venous access site and travel through veins to the sites where the leads' electrodes will be implanted or otherwise contact target coronary tissue. Electrodes for transvenously-placed leads can be implanted in the endocardium (the tissue lining the inside of the heart) of the right atrium or ventricle, or alternatively, in the branch vessels of the coronary venous system. In particular, lead electrodes can be implanted in the coronary sinus or a branch vessel thereof for sensing and/or stimulation of the left side of the heart (i.e., the left ventricle).

Various techniques have been used to facilitate fixation of the foregoing types of leads at the desired implantation sites. For leads partially implanted within the coronary venous system, fixation techniques should provide sufficient fixation to secure the lead in the desired implanted position, both acutely and chronically, without impeding delivery of the lead to the implantation site.

There is thus a continuing need in the art for a device and method for fixation of cardiac leads within the coronary vasculature which does not interfere with delivery of the lead and which can be deployed after delivery to provide acute and/or chronic fixation.

SUMMARY

According to an embodiment of the present invention, a medical electrical lead includes: a conductive lead body having a primary lumen adapted to receive a guiding member; at least one hydraulic lumen formed in an outer sheath of the lead body; at least one plunger slideably disposed in the at least one hydraulic lumen; and at least one fixation portion including at least one expandable fixation member. The fixation member includes a proximal end attached to an outer surface of the fixation portion and a distal end attached to the plunger disposed within the hydraulic lumen. The plunger is moveable in a distal direction from a first position to a second position. When the plunger is in a first, proximal position, the fixation member is in an expanded configuration.

According to another embodiment of the present invention, a fixation portion is provided as a separate member and is adapted to be coupled to the distal end of a medical electrical lead body. The fixation portion includes a hydraulic lumen in fluid communication with the hydraulic lumen on the lead body. The fixation portion also includes an inner lumen adapted to communicate with the primary lumen on the lead body.

According to another embodiment of the present invention, a medical electrical lead includes a lead body having an actuation lumen; a plunger slideably disposed in the actuation lumen; and a fixation member having a first end attached to the lead body and a second end attached to the plunger. The plunger is moveable between a first position and a second position.

A method of deploying a medical lead at a location within a vessel is also described. In general, the method includes: introducing fluid into a lumen formed within a lead body; collapsing at least one fixation member located on a fixation portion of the lead body; guiding a distal end of the lead body through a patient's vasculature to a target location with the patient's heart; releasing fluid from the lumen; and expanding the fixation member to secure the distal end of the lead body at the target location.

According to another embodiment of the present invention, a method of deploying a medical electrical lead to a location within a vessel includes introducing fluid into a lumen formed in a lead body and actuating a fixation member having a first end fixed to an outer surface of the lead body and a second end coupled to a plunger slideably disposed within the lumen.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 3A-3B are cross-sectional views of the portion of the lead shown in FIG. 2 according to an embodiment of the present invention.

FIG. 10A is a partial cross-sectional view of a portion of a lead including a preformed, expandable fixation member in an expanded configuration according to yet another embodiment of the present invention.

FIG. 10B is a partial cross-sectional view of a portion of lead including a preformed, expandable fixation member in a collapsed configuration according to yet another embodiment of the present invention.

Figure 1:
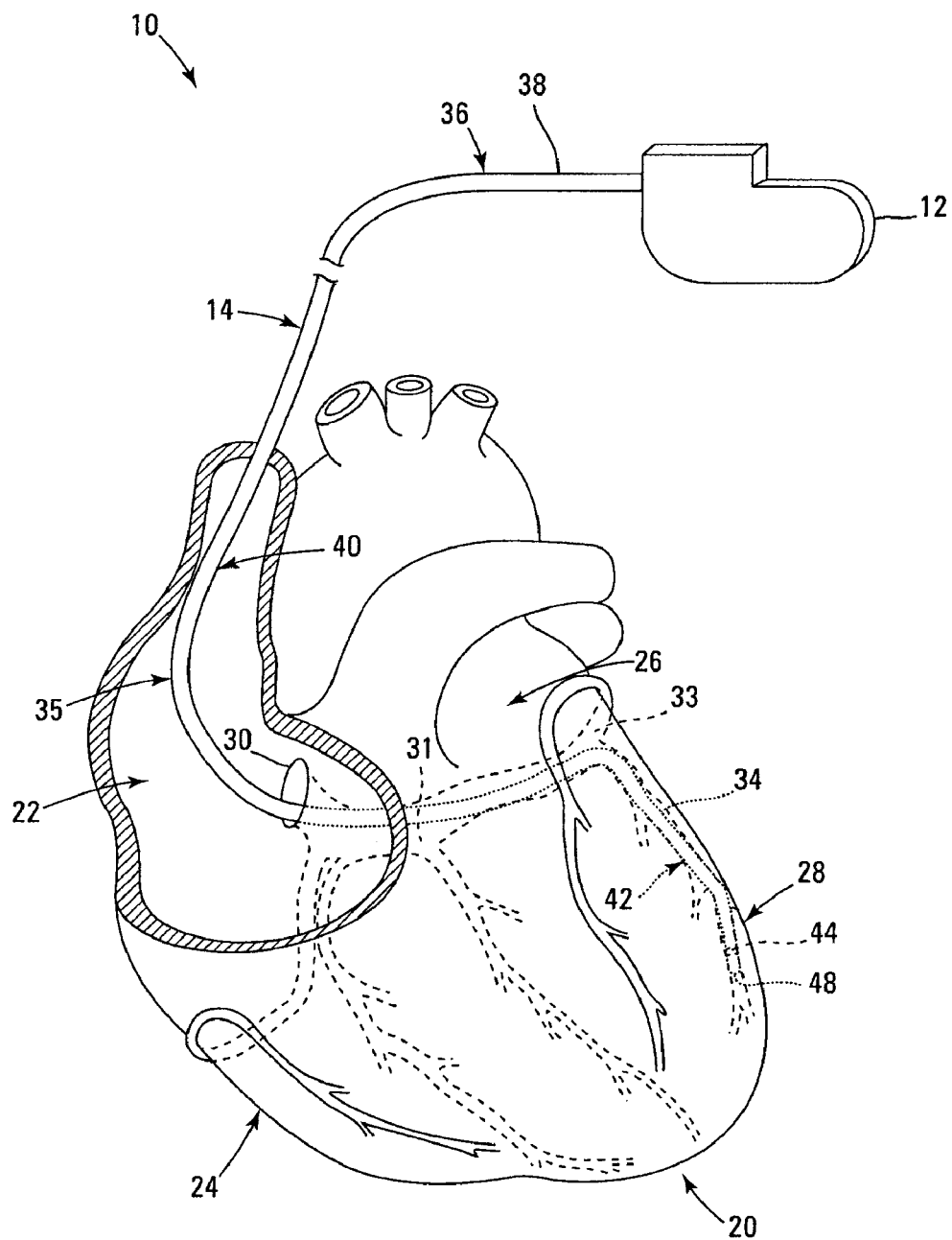
FIG. 1 is a schematic drawing of a cardiac rhythm management system including a pulse generator coupled to a lead deployed in a patient's heart according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 10 including a pulse generator 12 coupled to a medical electrical lead 14 deployed in a patient's heart 20, which includes a right atrium 22 and a right ventricle 24, a left atrium 26 and a left ventricle 28, a coronary sinus ostium 30 in the right atrium 22, a coronary sinus 31, and various coronary veins including a great cardiac vein 33 and other branch vessels off the coronary sinus 31 including an exemplary branch vessel 34.

As shown in FIG. 1, the medical electrical lead 14 includes an elongate body 35 defining a proximal portion 36 including a proximal end 38 and a distal portion 40. The distal portion 40 has a distal end portion 42 including at least one electrode 44 and terminating in a distal tip 48. In the embodiment illustrated in FIG. 1, the distal portion 40 is guided through the right atrium 22, the coronary sinus ostium 30, and the coronary sinus 31, and into the branch vessel 34 of the coronary sinus 31, with the distal end 42, and thus the electrode 44 and the distal tip 48, positioned within the branch vessel 34. The illustrated position of the lead 14 may be used, for example, for sensing physiologic parameters and delivering a pacing and/or defibrillation stimulus to the left side of the heart 20. Additionally, it will be appreciated that the lead 14 may also be partially deployed in other cardiac vessels such as the great cardiac vein 33 or other branch vessels for providing therapy to the left side of the heart 20.

Figure 2:
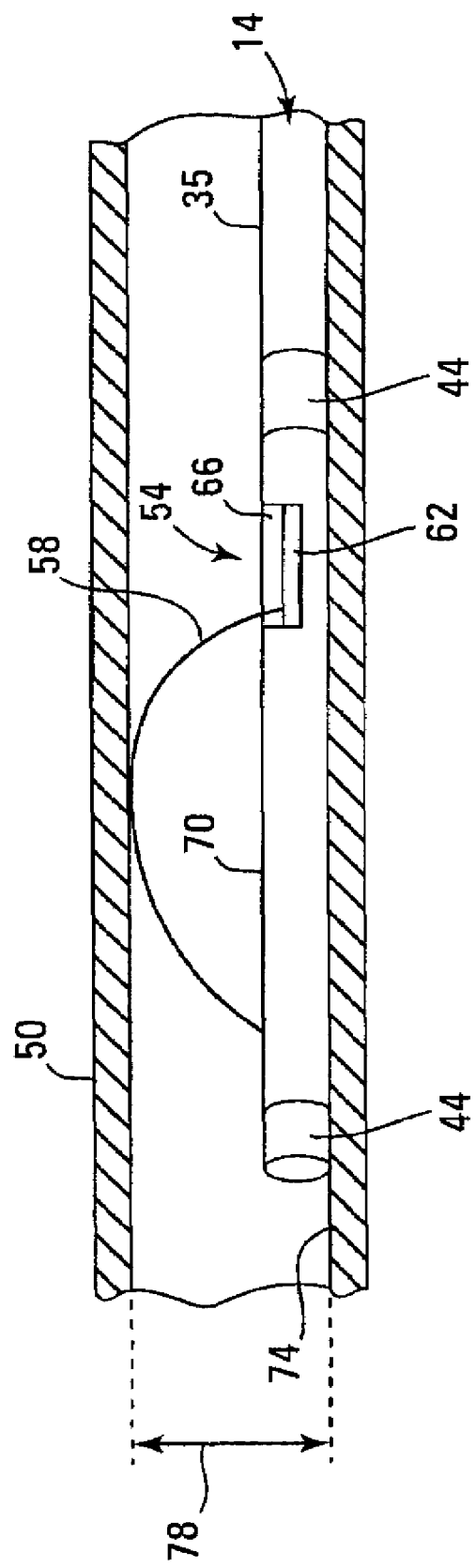
FIG. 2 is a schematic view of a portion of a lead according to an embodiment of the present invention deployed in a vessel.

FIG. 2 is a schematic view of the lead 14 deployed within a vessel 50 as shown in FIG. 1. As shown in FIG. 2, the lead 14 includes a fixation portion 54 including an expandable fixation member 58. The fixation portion 54 can be integrally formed in the lead body 35 or, alternatively, it can be provided as a separate member adapted to be coupled to the lead body 35. The fixation member 58 couples to a plunger 62 through a slot 66 located in an outer portion 70 of the fixation portion 54 on the lead body 35.

According to one embodiment of the present invention, the fixation member 58 is provided at a bias relative to one side of the lead body 35. In the expanded configuration, the fixation member 58 forces the lead body 35 into contact with the vessel wall 74 improving electrode contact at the target location. The fixation member 58 expands to a size determined by the inner diameter 78 of the vessel 50 and frictionally engages the vessel wall 74 to prevent, or substantially impede displacement and dislodgement of the distal end portion 42, and in particular, the electrode 44, from the branch vessel 34 or other target vessel. In some embodiments, these fixation members 58 advantageously provide acute fixation without interfering with delivery of the lead 14 to the desired implantation position. Additionally, if desired, the fixation members 58 can provide chronic fixation or, alternatively, can be adapted to permit repositioning and/or removal of the lead from the body when appropriate.

According to one embodiment of the present invention, the fixation portion 54 is provided in a distal end portion 42 of the lead body 35 in proximity to the electrode(s) 44. According to a further embodiment of the present invention the fixation portion is located proximal to the electrode 44 located at the distal end 42 of the lead body 35. In another embodiment, the fixation portion 54 is located distally to the electrode 44. In alternate embodiments of the present invention, the fixation portion 54 can be provided anywhere along the distal portion 40 of the electrical lead body 35.

The fixation member 58 can be an expandable strut, tine, leg, loop, cage, stent-like structure, or other expandable structure that is capable of frictionally engaging a vessel wall at the target location in a patient's heart 20. Additionally, the fixation member 58 can be made from a super-elastic, self-expanding, or a shape-memory material. The fixation member 58 can be made from a variety of materials including Nitinol or other nickel-titanium alloys, titanium, platinum or platinum alloys, MP35N alloy, SST, bio-compatible polymers, and combinations thereof. According to one embodiment of the present invention, the fixation member 58 is capable of assuming a preformed shape.

In one embodiment of the present invention, the fixation member 58 is nonconductive. In an alternate embodiment of the present invention, the fixation member 58 is conductive and is in electrical communication with a conductor 52. According to this embodiment the fixation member 58 can be used as an electrode.

According to another embodiment of the present invention, the fixation member 58 is provided with a coating, coating a portion of or the entire fixation member 58. In a further embodiment of the present invention, the coating permits and facilitates tissue in-growth around the fixation member 58 providing for chronic fixation. In an alternate embodiment, the coating prevents or slows tissue growth on or around the fixation member 58. An exemplary coating of this type is Teflon®.

FIGS. 3A-3B show a cross-sectional view of the electrical lead 14 according to one embodiment of the present invention. The drawings are not necessarily to scale and thus should not be limited to the relative dimensions provided in these and other figures. In one embodiment of the present invention, the lead body 35 is constructed of a conductive coil 80 sandwiched between an outer sheath 84 and an inner sheath 88. The inner sheath 88 defines a primary lumen 92. Alternatively, the conductive coil 80 can form the primary lumen 92. According to one embodiment of the present invention, the primary lumen 92 is open at the distal tip of the lead body 35. The primary lumen 92 is adapted to receive a guiding member such as a guide wire or a stylet for guiding the distal portion 40 of the lead 14 through a patient's vasculature. In an alternate embodiment, the guiding member is a guide catheter.

As shown in FIG. 2, one or more electrodes 44 are positioned along the lead body 35 and are in electrical communication with the coil 80 or other conductors located in the lead body 35. In one embodiment of the present invention, the lead 14 is bipolar. In alternate embodiments, the lead 14 is unipolar or includes multiple electrodes spaced apart from one another having the same polarity. Furthermore, a lead 14 provided in accordance with the present invention is not limited to the configuration described above. Rather, the lead 14 may have any configuration as is known in the art.

According to one embodiment of the present invention, as shown in FIGS. 3A-3B, the lead 14 also includes a hydraulic lumen 96, and a fixation portion 106 including a fixation member 110. The fixation portion 106 corresponds to the hydraulic lumen 96. The hydraulic lumen 96 can be formed in the outer sheath 84 of the lead 14. In alternate embodiments according to the present invention, one or more hydraulic lumens 96 are provided. The hydraulic lumen 96 extends from a proximal end 38 to a distal end portion 42 of the lead body 35. According to one embodiment of the present invention, the hydraulic lumen 96 is open at a distal end 114 to prevent an excess of pressure from building up within the lumen 96. According to an alternate embodiment, the distal end 114 is sealed. In the embodiment where the distal end is sealed, the pressure in the lumen 96 can be used to operate the fixation member 110. The hydraulic lumen 96 is adapted to receive and retain a fluid. The fluid is a bio-compatible, non-compressible fluid such as a saline or a sugar solution. The hydraulic lumen 96 is provided with an intake manifold provided in the proximal portion 36 of the lead 14. According to one embodiment of the present invention, an indeflator or syringe mates with the intake manifold and is used to inject fluid into the hydraulic lumen 96.

A plunger 118 is slideably disposed in the hydraulic lumen 96. According to one embodiment, when fluid is introduced into the hydraulic lumen 96 the hydraulic pressure in the hydraulic lumen 96 moves the plunger 118 in a distal direction from a first position to a second position located within the hydraulic lumen 96. When hydraulic pressure is released from the hydraulic lumen 96, the plunger 118 is capable of moving in a proximal direction from the second position back to the first position.

Figure 4A:
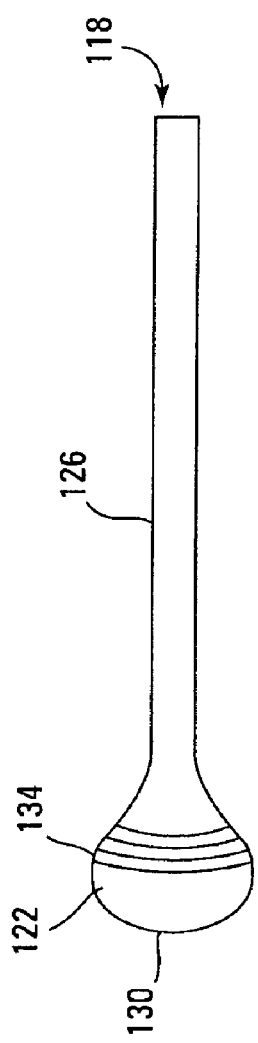
FIGS. 4A-4C are side plan views of plungers provided in accordance with various embodiments of the present invention.
Figure 4B:
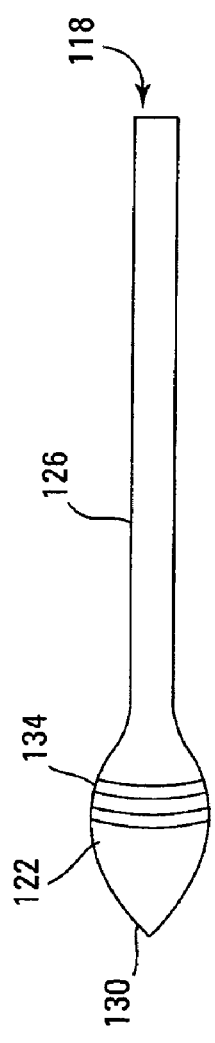
Figure 4C:
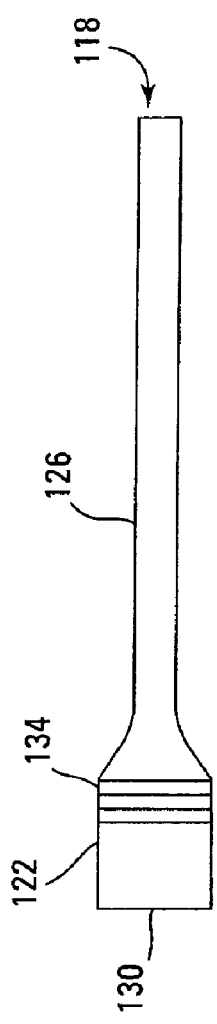

FIGS. 4A-4C are side plan views of a plunger 118 provided in accordance with various embodiments of the present invention. The plunger 118 includes a plunger head 122 and a plunger body 126. In one embodiment of the present invention the plunger 118 includes a flat, rounded or conical proximal end 130 and one or more annular ridges 134. The one or more annular ridges 134 allow the plunger head 122 to sealingly contact the inner wall of the hydraulic lumen 96 to form a seal capable of allowing pressure to build in the hydraulic lumen 96, and to move the plunger 118 in a distal direction from a first position to a second position. In an alternate embodiment, one or more sealing rings (e.g., O-rings) are provided on the plunger head 122. The seal between the plunger head 122 and the inner wall of the hydraulic lumen 96 can allow for some leakage of fluid to occur. Any loss in hydraulic pressure can be compensated for at the supply end of the hydraulic lumen 96. The plunger body 126 is tapered down from the plunger head 122 and is moderately flexible so as not to impart any additional stiffness on the lead body 35. The plunger 118 can be made from a variety of bio-compatible plastics or polymers as is known in the art.

As shown in FIGS. 3A-3B, the fixation member 110 includes a proximal end 140 attached to the outer portion 70 of the lead body 35 and a distal end 144 attached to the plunger 118 slideably disposed in the hydraulic lumen 96. A slot 148 is provided in the outer portion 70 of the lead body 35 allowing the distal end 144 of the fixation member 110 to communicate with the plunger 118 through the slot 148. The slot 148 is sufficiently sized such that as the plunger 118 moves from a first position to a second position, the slot 148 is capable of accepting the distal end 144 and/or a distal portion 152 of the fixation member 110 as the fixation member 110 expands and collapses. Additionally, in one embodiment of the present invention, the slot 148 can include a seal 150 to prevent bodily fluid from leaking into the lumen 96.

The fixation member 110 assumes a preformed expanded state prior to the introduction of fluid into the hydraulic lumen 96 and prior to insertion of the lead 14 into a patient's vasculature. As fluid is introduced into the hydraulic lumen 96, hydraulic pressure builds inside the lumen 96 pushing on the plunger head 122 causing the plunger 118 to move in a distal direction from a first, proximal position to a second, distal position. A shoulder or stop 156 is provided to prevent the plunger 118 from moving too far in a distal direction, preventing too much pull or tension from being placed on the proximal end 140 of the fixation member 110 attached to the outer portion 70 of the lead body 35. Additionally, the fixation member 110 itself also acts to prevent the plunger 118 from moving too far in a distal direction. As the plunger 118 slides in a distal direction indicated by the directional arrow in FIG. 3B, the fixation member 110 transitions or collapses from its preformed, expanded configuration (shown in FIG. 3A) to a collapsed configuration (shown in FIG. 3B). The lead 14 is then guided through the vasculature to a target location within a patient's heart 20. Once the lead 14 has reached the target location, hydraulic pressure is released from the hydraulic lumen 96 allowing the preformed, self-expanding fixation member 110 to spontaneously transition from its collapsed configuration to its expanded configuration. As the fixation member 110 transitions, the distal end 144 of the fixation member 110 pulls on the plunger 118, causing the plunger 118 to slide from its second, distal position to its first, proximal position. The release of fluid can be controlled thereby allowing for a controlled deployment of the fixation member 110, if desired. When the plunger 118 is in a first proximal position, the fixation member 110 is in its preformed, expanded configuration. When the plunger 118 moves in a distal direction upon the application of hydraulic pressure, the distal end 144 of the fixation member 110 is pulled distally into the slot 148 collapsing the fixation member 110. In one embodiment of the present invention, the distal end 144 of the fixation member 110 is pulled such a distance that the slot 148 receives a distal portion 152 of the fixation member 110 in addition to the distal end 144.

According to an alternate embodiment of the present invention, the hydraulic actuation of the fixation member 110 can operate conversely to the operations described in the above paragraph. In the alternate embodiment of the present invention, hydraulic pressure can be applied to transition the fixation member 110 from a collapsed configuration to an expanded configuration. Pressure in the hydraulic lumen 96 is maintained by sealing the lumen 96 at the proximal end or the fluid introduction site using an appropriate sealing means. Pressure is maintained in the lumen until tissue ingrowth has taken place and the chronic fixation has occurred. Release of pressure from the lumen 96 allows the fixation member 110 to transition from its expanded configuration back to its collapsed configuration. In one embodiment, the hydraulic lumen 96 is configured such that pressure can release over a desired period of time. According to one exemplary embodiment, the hydraulic lumen 96 is configured such that the release of pressure occurs over a time period ranging from a few days to several weeks.

Figure 5A:
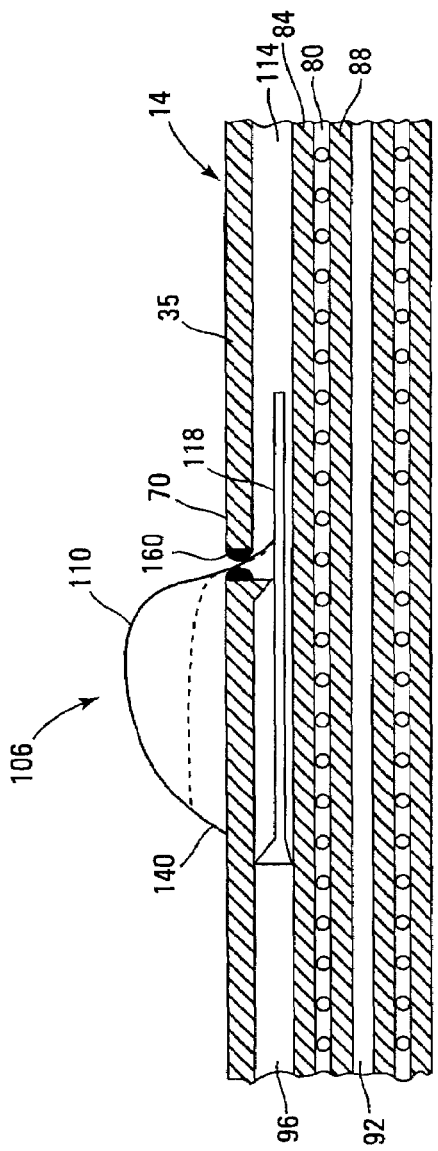
FIG. 5A is a cross-sectional view of a portion of a lead including a preformed, self-expanding fixation member in an expanded configuration according to one embodiment of the present invention.
Figure 5B:
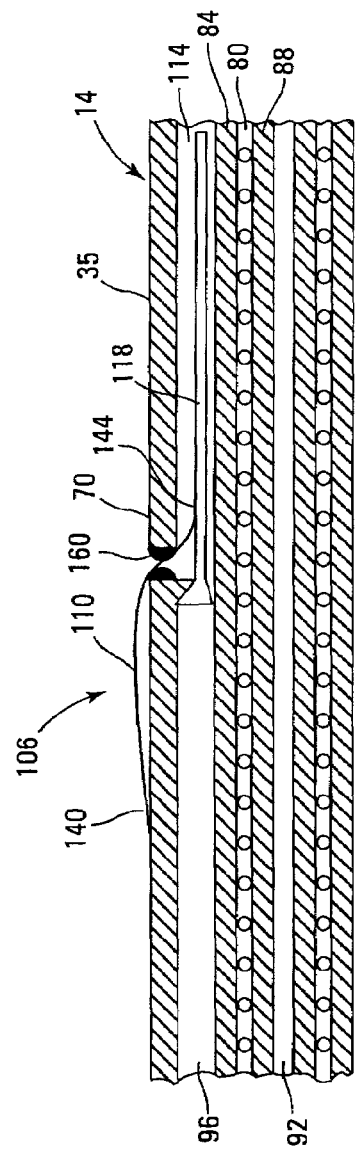
FIG. 5B is a cross-sectional view of a portion of a lead as shown in FIG. 5A including the preformed, self-expanding fixation member in a collapsed configuration according to one embodiment of the present invention.

FIGS. 5A and 5B show a portion of a lead 14 according to yet another embodiment of the present invention. According to the embodiment shown in FIGS. 5A and 5B, the fixation member 110 couples to the plunger 118 through a seal 160 provided in the outer portion 70 of the lead body 35. The seal is configured such that it prevents bodily fluid from entering the lumen 96 and is adapted to assist in maintaining hydraulic pressure within the lumen 96. The seal is made from any biocompatible material as is known in the art.

Figure 6:
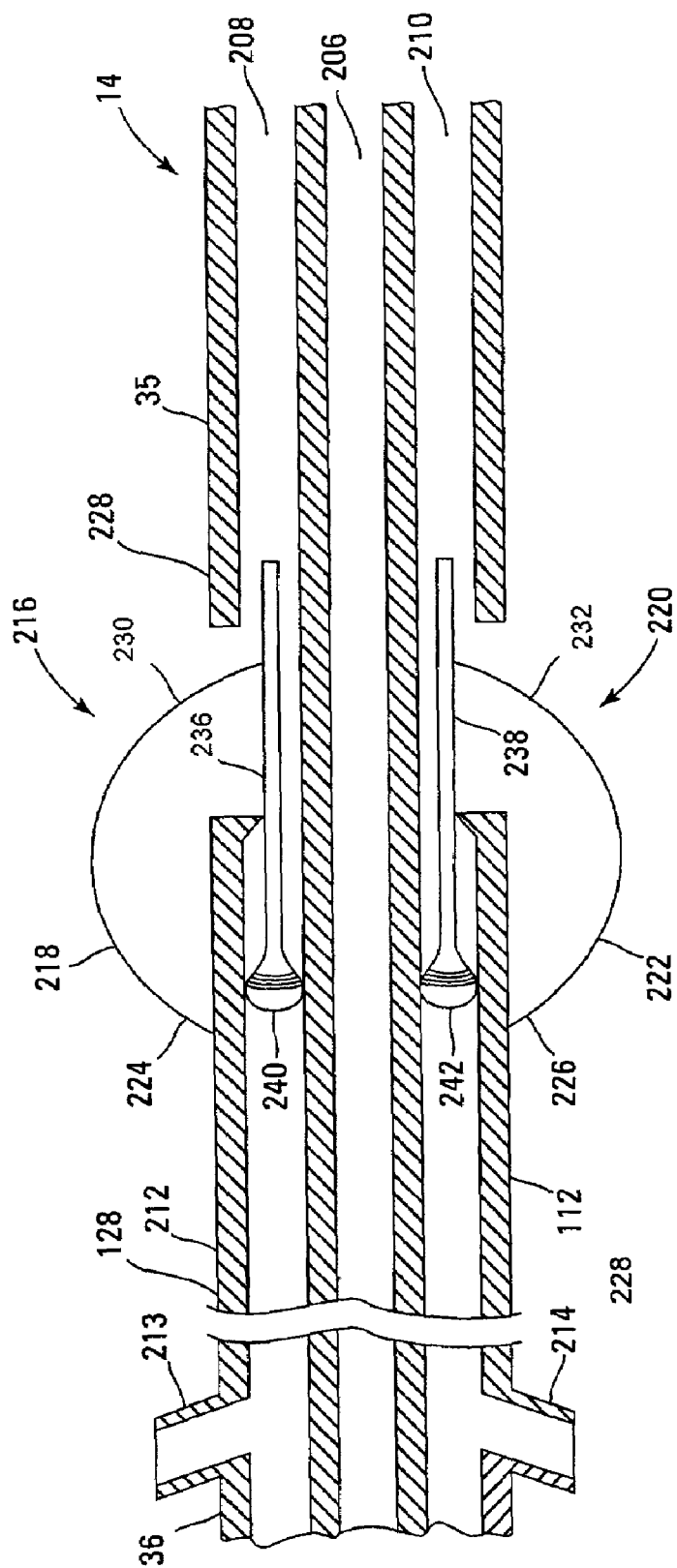
FIG. 6 is a cross-sectional view of a lead including a preformed, self-expanding fixation member in an expanded configuration according to another embodiment of the present invention.

FIG. 6 is a cross-sectional view of the lead 14 according to another embodiment of the present invention. As shown in FIG. 6, the lead 14 includes a primary lumen 206, a first hydraulic lumen 208, and a second hydraulic lumen 210. The hydraulic lumens 208, 210 are separately formed in the outer sheath 212 of the lead 14 and are spaced an equal distance from one another. The hydraulic lumens 208, 210 extend from a proximal end 36 of the lead 14 to a distal end portion of the lead body 35. Each lumen 208, 210 is provided with its own manifold 213, 214 located at the proximal end 36 of the lead 14 for receiving a fluid from a device such as syringe or an indeflator. The fluid is a non-compressible, biocompatible fluid such as saline or a sugar solution.

The lead 14 also includes a first fixation portion 216 including a first fixation member 218 and a second fixation portion 220 including a second fixation member 222. The fixation members 218 and 222 include proximal ends 224, 226 secured to an outer surface 228 of the lead body 35 and distal ends 230, 232 connected to plungers 236, 238 slideably disposed within the hydraulic lumens 208, 210. When a fluid is introduced into either of the hydraulic lumens 208, 210, hydraulic pressure pushes on the plunger heads 240, 242 causing the plungers 236, 238 to move in a distal direction from a first proximal position to a second, distal position. By providing for separate hydraulic lumens 208, 210, the fixation members 218, 222 need not be actuated simultaneously, but allow for the flexibility in selectively actuating the fixation members 218, 222 as deemed appropriate by one having skill in the art. The flexibility in providing separately activated fixation members 218, 222, also allow for flexibility in positioning the lead body 35 at a target location in a patient's body to improve electrode contact with a vessel wall. For example, a stenosis located on one vessel wall may impede electrode contact with the wall despite the fact that the actuated fixation member 218 or 222 is provided at a bias to a longitudinal axis of the lead body. The fixation member 218 or 222 can be collapsed allowing the lead to be repositioned at the target location. The other fixation member 218 or 222 can be actuated, forcing the lead body 35 to come in contact with the opposite vessel wall. Additionally, according to another embodiment of the present invention, the fixation portions 216, 220 can be provided in different portions of the lead body 35. For example, fixation portion 220 can be located distally to fixation portion 216. The locations of the fixation portions 216, 220 can be selected based on a patient's needs and anatomy as determined by one having skill in the art.

In alternate embodiments of the present invention, multiple hydraulic lumens are formed in the outer sheath 84 of the lead 14. According to various embodiments of the present invention, a lead 14 has two, three or even four hydraulic lumens formed in the outer sheath 84. In each embodiment, the hydraulic lumens correspond to a fixation portion. Generally, the fixation portions are spaced an equal distance from one another. The fixation portions can be located in the same region of the lead body 35 or in different regions.

Figure 7:
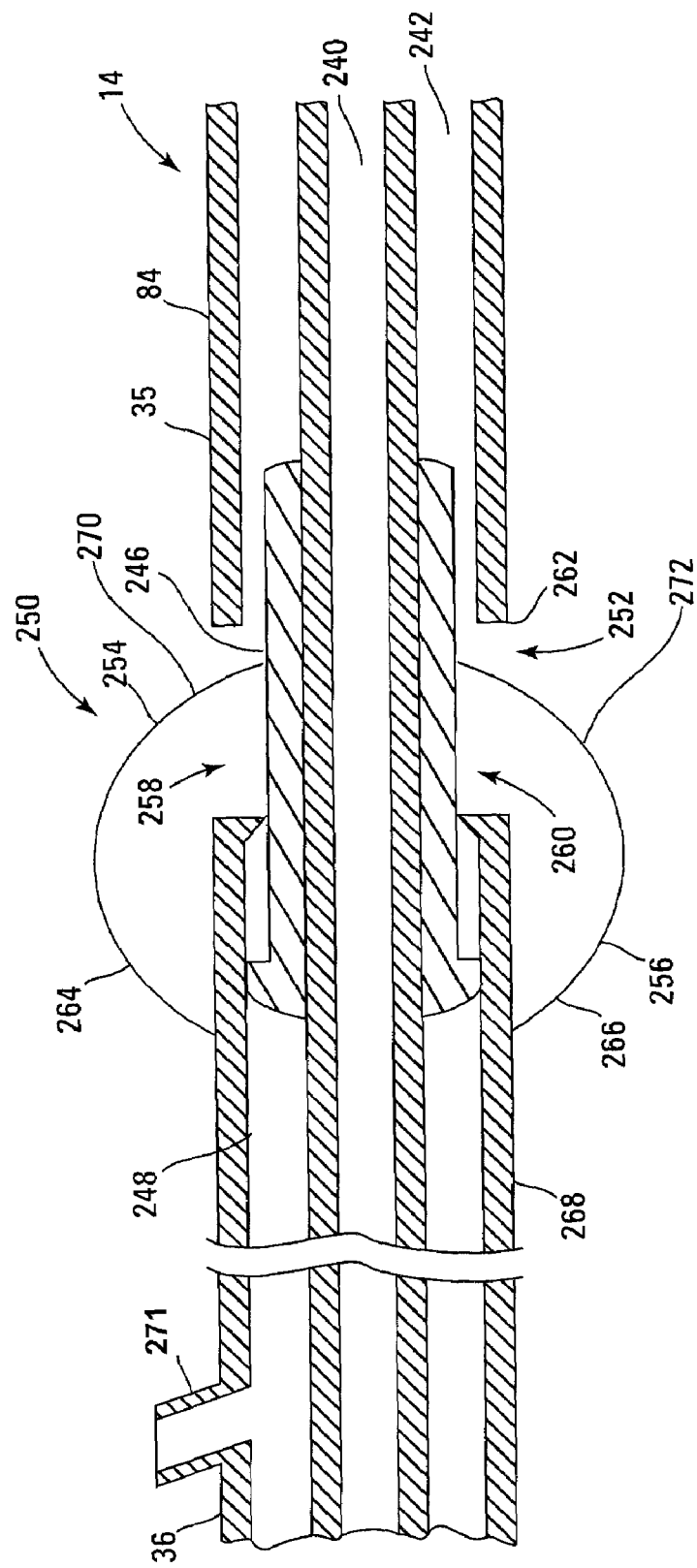
FIG. 7 is a cross-sectional view of a lead including a preformed, self-expanding fixation member in an expanded configuration according to yet another embodiment of the present invention.

FIG. 7 shows the lead according to yet another embodiment of the present invention. As shown in FIG. 7, the lead 14, includes a primary lumen 240 and an annular hydraulic lumen 242. According to this embodiment, the annular lumen 242 is formed in the outer sheath 84 of the lead 14. A barrel or cylindrically shaped plunger 246 is slideably disposed within the hydraulic lumen 242. The cylindrically shaped plunger 246 includes at least one annular ridge or O-ring allowing the plunger 246 to sealingly contact the inner wall 248 of the hydraulic lumen 242. The lead 14 also includes at least one fixation portion 250. In the embodiment shown in FIG. 7, the lead 14 includes two fixation portions 250, 252. The fixation portions 250, 252 include fixation members 254, 256. According to one embodiment of the present invention, the fixation members are radially expanding struts. In alternate embodiments of the present invention, the fixation members can assume a variety of self-expanding structures. Fixation members 254, 256 communicate with the plunger 246 through slots 258, 260 formed in an outer surface 262 of the lead body 35. The fixation members 254, 256 include proximal ends 264, 266 attached to an outer surface 262 of the lead body 35 and distal ends 270, 272 attached to the plunger 246. According to one embodiment of the present invention, the fixation portions 250, 252 are provided in a distal end portion 42 of the lead body 35. In an alternate embodiment of the present invention, the fixation portions 250, 252 are provided anywhere along the distal portion 40 of the lead body 35.

The fixation members 254, 256 assume a preformed open or expanded state prior to the introduction of fluid into the hydraulic lumen 242 and prior to insertion of the lead 14 into a patient's vasculature. As fluid is introduced into the hydraulic lumen 242 via a manifold 271 located in the proximal end 36 of the lead 14, hydraulic pressure builds inside the lumen 242 pushing on the plunger 246 causing the plunger 246 to move in a distal direction from a first, proximal position to a second, distal position. As the plunger 246 slides in a distal direction, the fixation members 254, 256 simultaneously transition or collapse from their preformed, expanded configuration to a collapsed configuration. The lead 14 is then guided through the vasculature to a target location within a patient's heart 20. Once the lead 14 has reached the target location, hydraulic pressure is released from the hydraulic lumen 242 allowing the preformed, self-expanding fixation members 254, 256 to spontaneously transition from their collapsed configurations to their expanded configurations. As the fixation members 254, 256 transition, the distal ends 270, 272 of the fixation members 254, 256 pull on the plunger 246, causing the plunger 246 to slide from its second, distal position to its first, proximal position. The release of fluid can be controlled thereby allowing for a controlled deployment of the fixation members 254, 256, if desired. When the plunger 246 is in a first proximal position, the fixation members 254, 256 are in their preformed, expanded configuration.

Figure 8A:
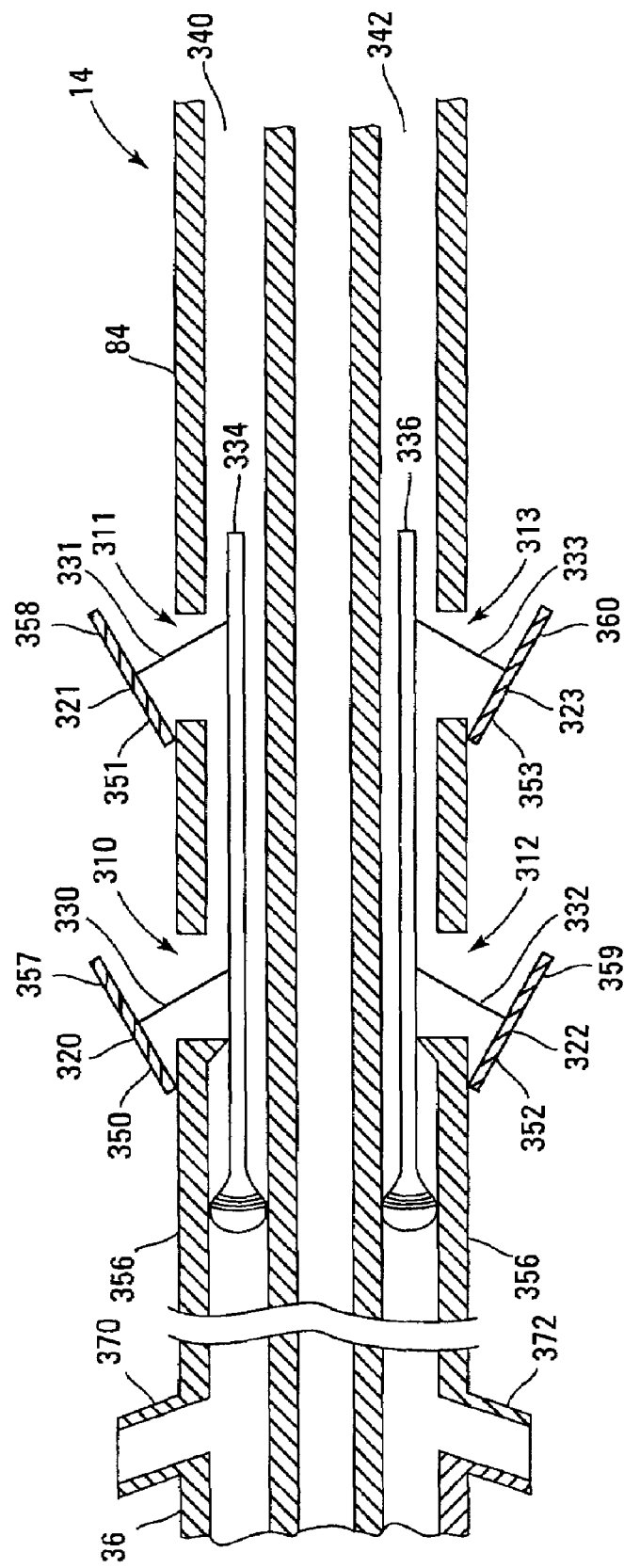
FIG. 8A is a cross-sectional view of a portion of a lead including multiple preformed, expandable fixation members in an expanded configuration according to an embodiment of the present invention.
Figure 8B:
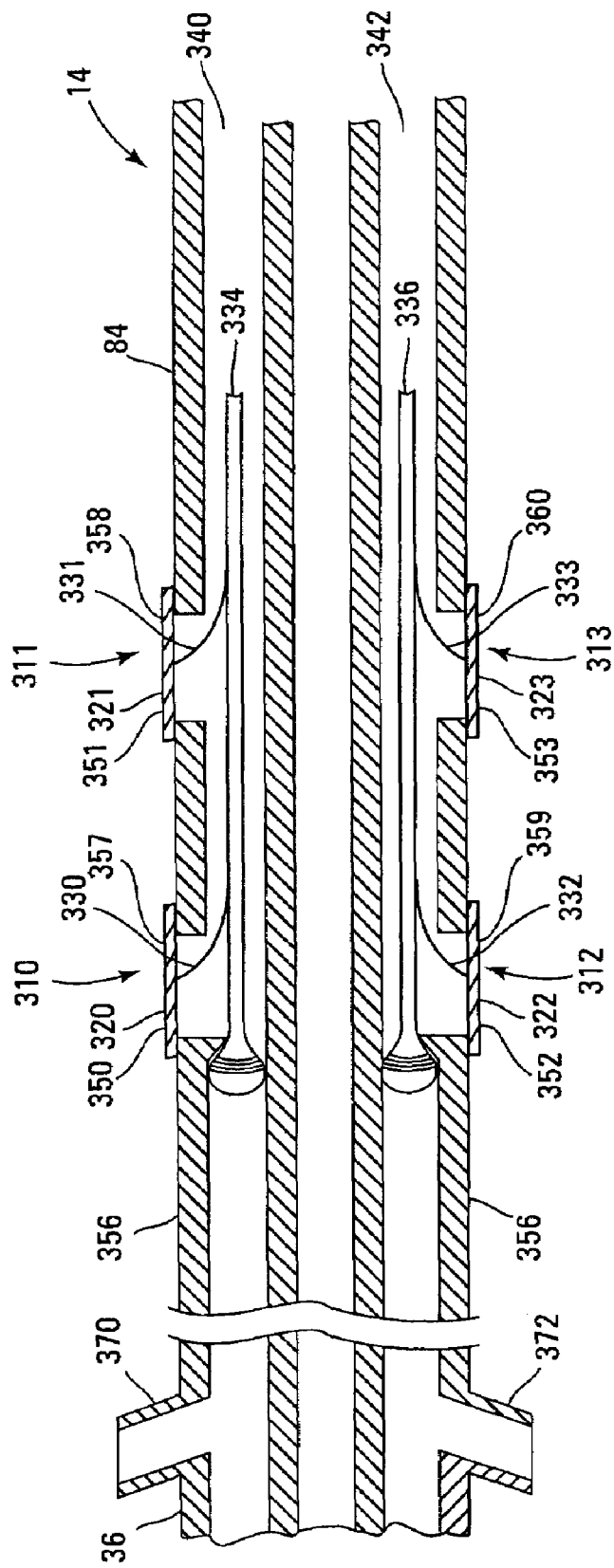
FIG. 8B is a cross-sectional view of a portion of a lead including multiple preformed, expandable fixation members in a collapsed configuration according to an embodiment of the present invention.

According to one embodiment of the present invention, shown in FIGS. 8A-8B, the lead 14 includes four fixation portions 310-313 each including a fixation member 320-323. As shown in FIGS. 8A-8B, the fixation members 320-323 are expandable tines. Each tine 320-323 includes a tether 330-333 that is in communication with a plunger 334, 336 slideably disposed within a hydraulic lumen 340, 342 formed in an outer sheath 84. In the embodiment shown in FIGS. 8A-8B, two separate hydraulic lumens 340, 342 are formed in the outer sheath 84 and are spaced an equal distance from one another. Plungers 334, 336 are slideably disposed within their respective hydraulic lumens 340, 342. The expandable tines 320-323 are in the expanded configuration prior to insertion of the lead 14 in a patient's vasculature. The expandable tines 320-323 include proximal ends 350-353 attached to an outer surface 356 of the lead body 35 and mid-portions 357-358 attached to a proximal end of the tethers 330-333. In each fixation portion, the distal end of the tethers 330-333 communicate through individual slots provided in an outer sheath 84 of the lead 14 and are coupled to plungers 334, 336 slideably disposed within hydraulic lumens 340, 342. The slots are adapted to receive a distal end and/or a distal portion of the tethers 330-333 connected to the tines 320-323. As fluid is introduced into the hydraulic lumens 340, 342 through manifolds 370, 372 located at the proximal end 36 of the lead body 35, hydraulic pressure pushes on the plungers 334, 336 causing them to move in a distal direction from a first, proximal position, to a second, distal position collapsing the tines 320-323. Separate hydraulic lumens 340, 342 allow for the selective actuation of the tines 320-323 located on either side of the lead body 35. This allows flexibility in deploying and positioning the lead 14 in a patient's vasculature and may facilitate removal of the lead 14. Additionally, the fixation portions 310-313 need not be located symmetrically on the lead body 35 to one another, but rather one fixation portion can be located distally to the other. In an alternate embodiment of the present invention the hydraulic lumen is an annular hydraulic lumen and the plunger is a cylindrical plunger. In the alternate embodiment, the fixation members 320-323 are simultaneously actuated between an expanded configuration and a collapsed configuration.

Figure 9A:
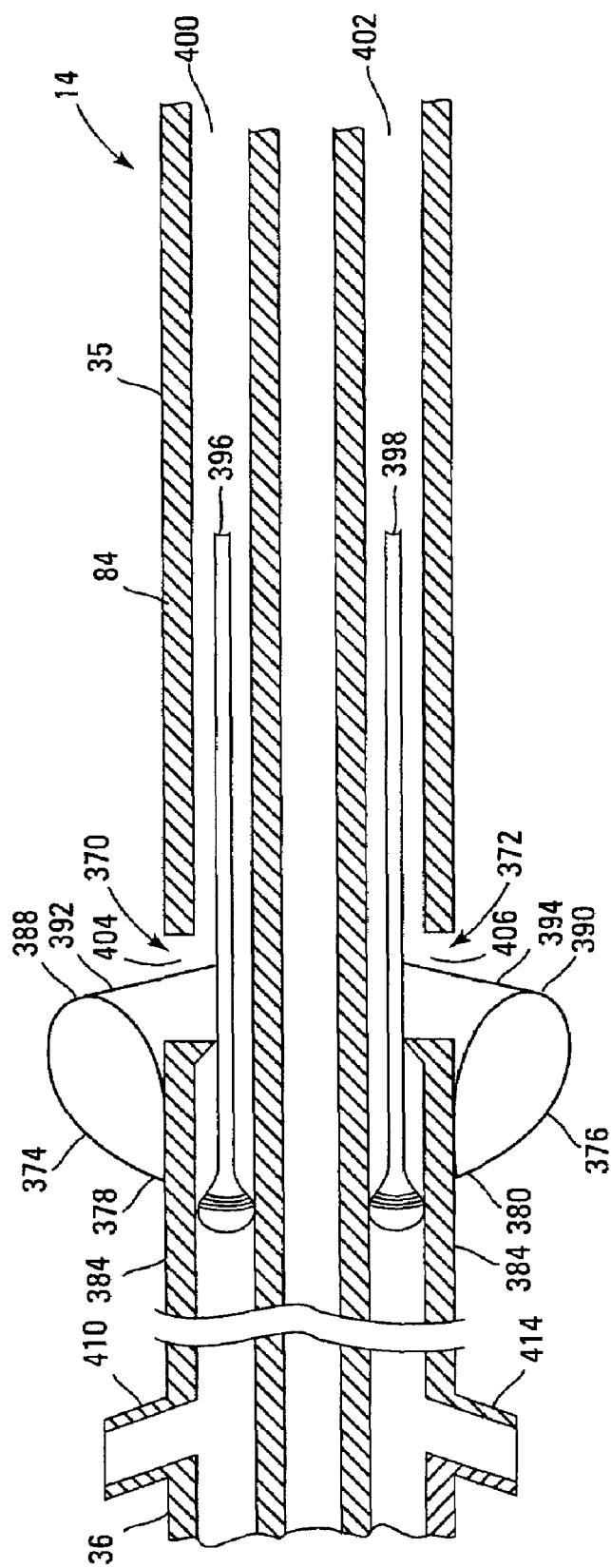
FIG. 9A is a cross-sectional view of a portion of a lead including multiple preformed, expandable fixation members in an expanded configuration according to another embodiment of the present invention.
Figure 9B:
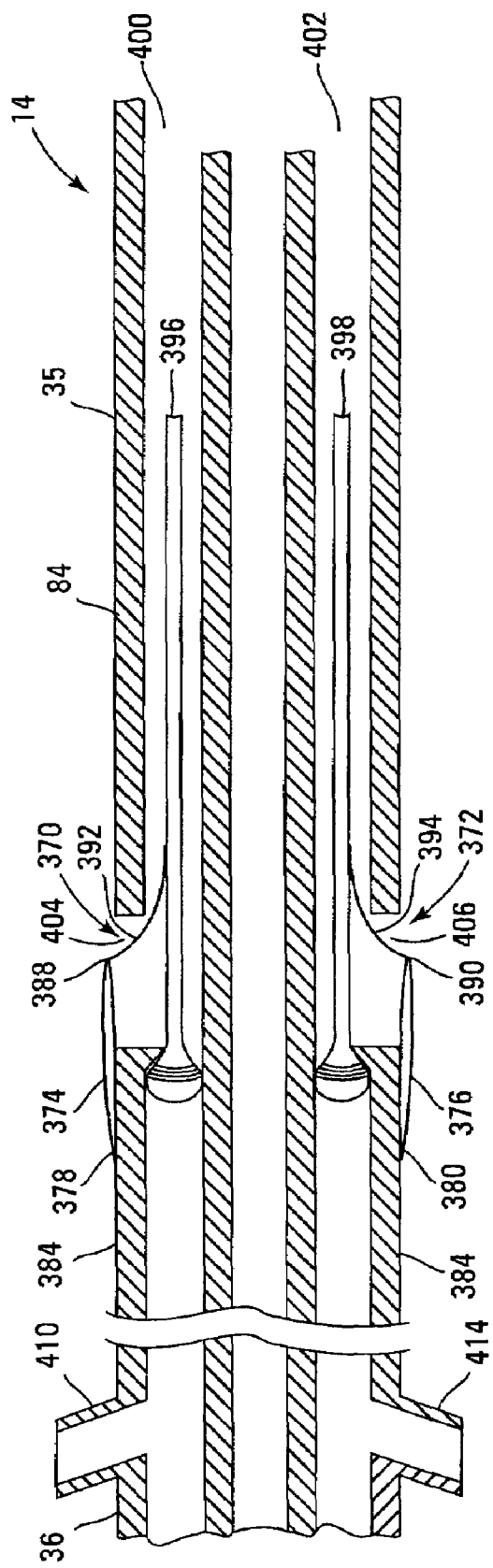
FIG. 9B is a cross-sectional view of a portion of a lead including multiple preformed, expandable fixation members in a collapsed configuration according to another embodiment of the present invention.

According to another embodiment of the present invention, as shown in FIGS. 9A-9B, the lead 14 includes one or more fixation portions 370, 372, wherein the fixation members 374, 376 are loops. The loops 374, 376 have a preformed, expanded configuration. Similar to the embodiment where the fixation member was a tine, the loops 374, 376 include proximal ends 378, 380 attached to an outer surface 384 of the lead body 14 and distal ends 388, 390 attached to proximal ends of tethers 392, 394. The tethers 392, 394 are coupled to plungers 396, 398 slideably disposed within hydraulic lumens 400, 402 separately formed in an outer sheath 84 of the lead 14. The tethers 392, 394 coupling the loops 374, 376 to the plungers 396, 398 communicate with the plungers 396, 398 through individual slots 404, 406 provided in the outer sheath 84. The slots 404, 406 are adapted to receive a distal end and/or a distal portion of the tethers 392, 394 connected to the loops 374, 376. As fluid is introduced into the hydraulic lumens 400, 402 through manifolds 410, 414 located at the proximal end 36 of the lead body 35, hydraulic pressure pushes on the plungers 396, 398 causing the plungers 396, 398 to move in a distal direction from a first, proximal position, to a second, distal position collapsing the loops 374, 376 from their preformed expanded configuration (shown in FIG. 9A) to a collapsed configuration (shown in FIG. 9B). Separate hydraulic lumens allow for the selective actuation of the loop or loops located on either side of the lead body 35. This allows flexibility in deploying and positioning the lead 14 in a patient's vasculature and can facilitate removal of the lead. Additionally, the fixation portions 370, 372 need not be located symmetrically on the lead body 35 to one another, but rather one fixation portion can be located distally to the other. According to another embodiment of the present invention, the lead 14 includes three or four fixation portions located on the lead body 35. In a further embodiment of the present invention, the hydraulic lumen is an annular hydraulic lumen and the plunger is a cylindrical plunger. In the alternate embodiment, the fixation members are simultaneously actuated between an expanded state and a collapsed state.

FIGS. 10A and 10B show the lead according to yet another embodiment of the present invention. As shown in FIGS. 10A-10B, the fixation member 420 is a preformed, self-expanding stent-like structure. The fixation member 420 includes a proximal ring 424 secured to an outer surface 428 of the lead body 35. The fixation member 420 also includes a distal ring 430 including one or more tethers 434 coupled to a cylindrical plunger 436 slideably disposed within an annular hydraulic lumen 438 formed in an outer sheath 84. The distal ring 430 is slideably disposed over an outer surface 428 of the outer sheath 84. The tethers 434 communicate with the plunger 436 through individual slots 440, 442 provided in the outer sheath 84. Prior to insertion of the lead 14 into a patient's vasculature, the stent-like fixation member 420 is in a preformed, expanded configuration (shown in FIG. 10A). As hydraulic pressure is introduced into the hydraulic lumen 438, pressure builds forcing the plunger 436 to move in a distal direction from a first, proximal position to a second, distal position. The tethers 434 coupled to the plunger 436 pull on the distal ring 430 slideably disposed over the sheath 84, causing the stent-like fixation 420 member to transition from its preformed, expanded configuration (shown in FIG. 10A) to a collapsed configuration (shown in FIG. 10B). The stent-like fixation member 420 is capable of expanding such that it expands with enough force to frictionally engage an inner diameter of the vessel so as to secure the lead 14 in place at the target location. According to an embodiment of the present invention, the stent-like fixation member 420 includes a coating to promote fibrosis in and around the fixation member 420.

Figure 11:
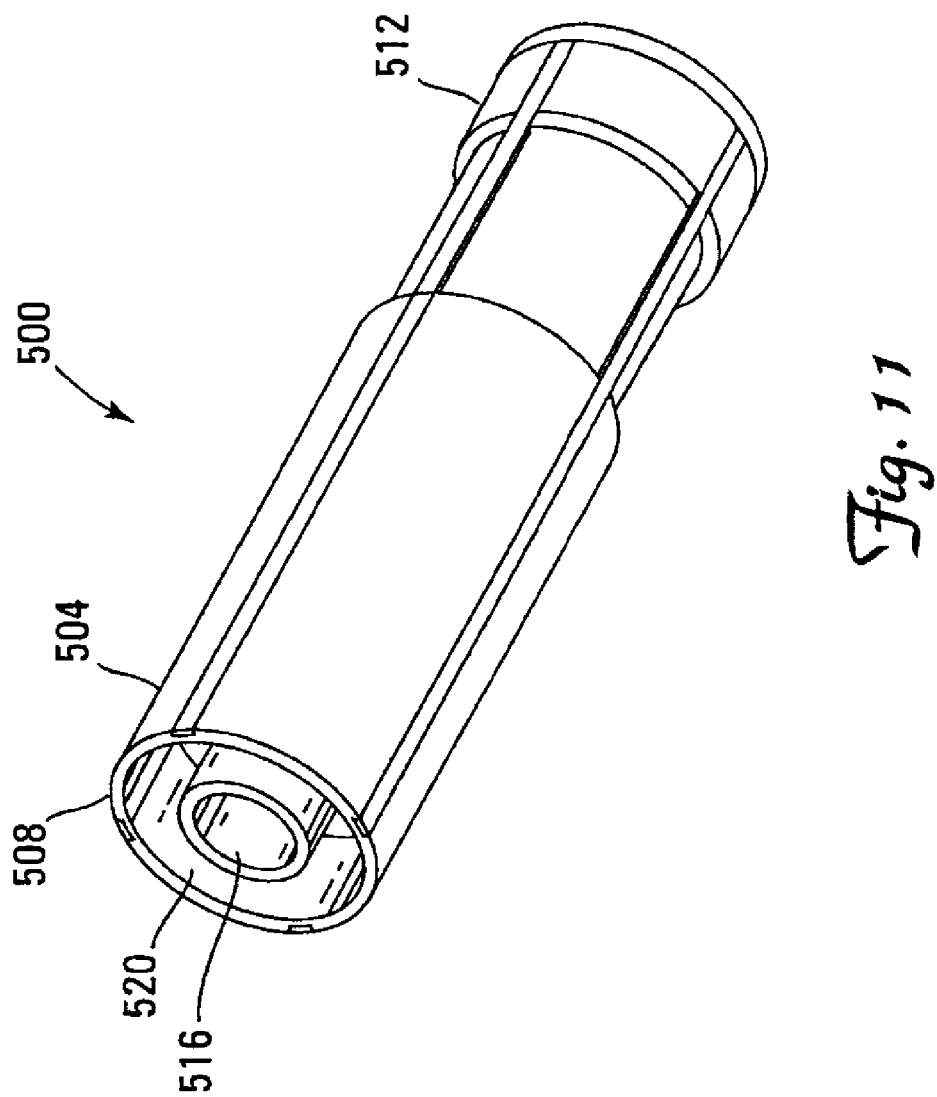
FIG. 11 is a side plan view of a fixation portion located along a lead body according to yet another embodiment of the present invention.
Figure 12A:
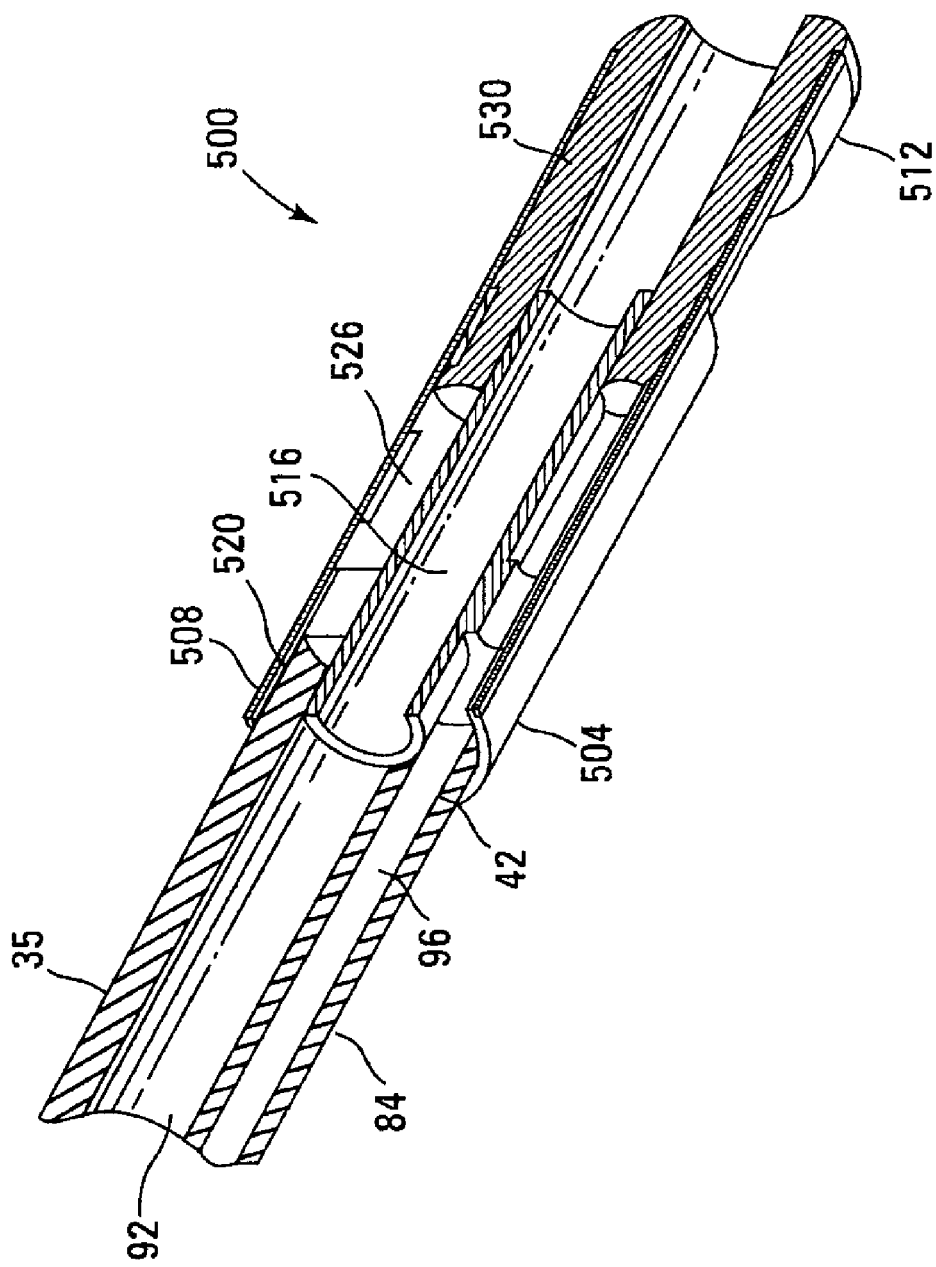
FIG. 12A is a partial cross-sectional view of the fixation portion shown in FIG. 11 coupled to a lead body and including more than one preformed, self-expanding fixation members in a collapsed configuration according to yet another embodiment of the present invention.
Figure 12B:
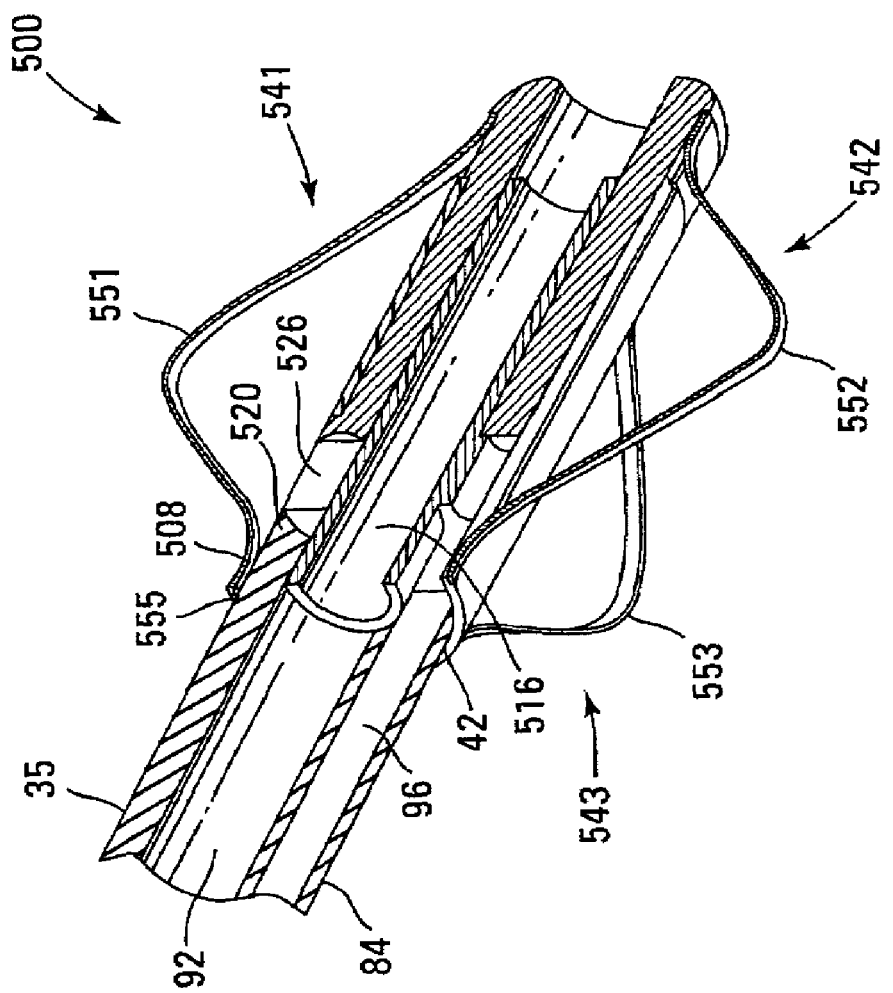
FIG. 12B is a partial cross-sectional view of the fixation portion shown in FIG. 11 coupled to a lead body and including more than one preformed, self-expanding fixation members in an expanded configuration connected to a lead according to yet another embodiment of the present invention.
Figure 13:
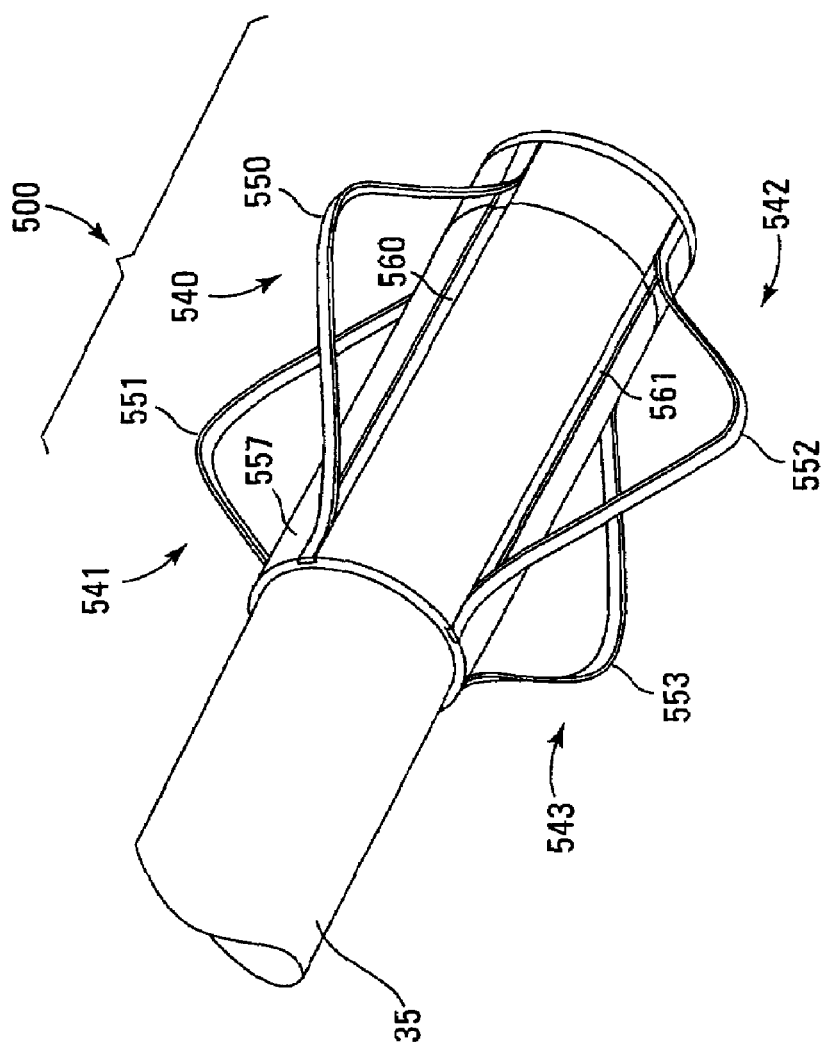
FIG. 13 is a perspective view of the fixation portion shown in FIG. 12 including more than one preformed, self-expanding fixation members in an expanded configuration connected to a lead body according to an embodiment of the present invention.

FIGS. 11-13 show a fixation portion 500 provided in accordance with yet another embodiment of the present invention. The fixation portion 500 is provided as a separate member adapted to be coupled to the distal end 42 of the lead body 35. As shown in FIG. 11, the fixation portion 500 includes a proximal portion 504 including a coupling portion 508, a distal portion 512, and an inner lumen 516. In one embodiment of the present invention, the coupling portion 508 is sized such that its outer diameter is larger than an outer diameter of the lead body 35 to which the fixation portion 500 can be coupled. The coupling portion 508 also includes an annular space 520 sized to receive the distal end 42 of the lead body 35. In an alternate embodiment of the present invention, the coupling portion 508 is flared. When the fixation portion 500 is coupled to the distal end 42 of the lead body 35, the coupling portion 508 overlaps the distal end 42 providing a snug-tight fit as the inner diameter of the coupling portion 508 generally corresponds to the outer diameter of the distal end 42 of the lead body 35. According to one embodiment of the present invention, an inner surface of the coupling portion 508 of the fixation portion 500 and/or the outer surface of the distal end 42 of the lead body 35 is provided with a bonding means (e.g. adhesive) for securing the coupling portion 508 to the distal end 42. Additional mating members may also be provided.

FIGS. 12A and 12B are cross-sectional drawings of a the fixation portion 500 shown in FIG. 11 coupled to a distal end 42 of a lead body 35. An exemplary lead body is described and shown in FIGS. 3A and 3B. FIG. 13 is a perspective view of the fixation portion 500 coupled to a lead body 35 as shown in the cross-section in FIGS. 12A-12B. As shown in FIGS. 12A and 12B, the fixation portion 500 also includes an annular hydraulic lumen 526 and a cylindrical or barrel-shaped plunger 530 disposed within the annular hydraulic lumen 526. In one exemplary embodiment of the present invention, the annular lumen 526 also includes a shoulder or stop for preventing the cylindrical plunger 530 from moving too far in a distal direction. Alternatively the movement of the cylindrical plunger 530 can be limited by the length of the fixation members to which it is attached. The annular hydraulic lumen 526 is in fluid communication with at least one hydraulic lumen 96 formed in the outer sheath 84 of the lead body 35, as described in the previous embodiments, and is adapted to receive and retain a non-compressible, biocompatible fluid. Additionally, the inner lumen 516 of the fixation portion 500 is in communication with the primary lead lumen 92 of the lead body 35. According to an embodiment of the present invention, the inner lumen 516, in communication with the main lead lumen 92, is adapted to receive a guiding member such as a guide wire or a stylet for positioning the fixation portion 500 at a target location within a patient's heart.

As shown in FIGS. 12B and 13, the fixation portion 500 includes one or more preformed, self-expanding fixation members. According to one embodiment of the present invention, as best shown in FIG. 13, the fixation portion 500 includes four fixation portions 540-543. The four fixation portions 540-543 are spaced an equal distance apart from one another and each include a preformed, self-expanding fixation member 550-553, respectively. As best shown in FIGS. 12B and 13, the fixation members 550-553 are struts having a preformed, expanded configuration. Each strut 550-553 includes a proximal end attached to an outer surface 555 of the fixation portion 500 and a distal end attached to a cylindrical plunger 530 slideably disposed within the annular hydraulic lumen 526. The struts 550-553 communicate with the plunger 530 through separate slots (not shown) formed in the outer sheath 555 of the fixation portion 500. Additionally, according to an embodiment of the present invention each of the struts 550-553 translate along grooves formed in an outer surface 557 of the outer sheath 555 as they transition from an expanded state to a collapsed state. Exemplary grooves 560 and 561 are best viewed in FIG. 13. In the collapsed configuration the grooves 560, 561 allow the fixation members 550-553 to lie flush with the outer surface 557 of the fixation portion 500. According to one exemplary embodiment, the movement of the cylindrical plunger 530 is limited by the length of the struts 550-553 to which it is attached. The struts 550-553 preformed shape controls the movement of the plunger 530 such that an additional stop of shoulder located within the hydraulic lumen is not required.

As fluid is introduced into the hydraulic lumen 96 through a manifold (not shown) located at the proximal end 36 of the lead body 35, fluid flows from the hydraulic lumen 96 located in the lead body 35 into the annular hydraulic lumen 526 formed in the fixation portion 500. Hydraulic pressure builds within the lumen 526 and pushes on the plunger 530 causing the plunger 530 to move in a distal direction from a first, proximal position, to a second, distal position simultaneously collapsing the struts 550-553. The distal end 42 of the lead body 35 including the fixation portion 500 can then be positioned at the target location within a patient's body. Once the target location has been reached and the distal end 42 placed in the desired position, hydraulic pressure can be released from the hydraulic lumens 96 and 526, thereby allowing the struts 550-553 to transition from their collapsed configuration (shown in FIG. 12A) to their expanded configuration (shown in FIGS. 12B and 13), securing the distal end 42 of the lead 14 in position within a vessel 50.

The distal end 42 of the lead 14 can be repositioned by reintroducing fluid and pressure into the hydraulic lumens 96 and 526, thereby collapsing the fixation members 550-553 on the fixation portion 500. The fixation members 550-553 are allowed to re-expand by releasing hydraulic pressure from the lumens 96, 526 once a new position has been achieved. The introduction and release of hydraulic pressure from the hydraulic lumens 96, 526 can be controlled thus allowing for a controlled actuation of the fixation members 550-553.

Prior to inserting the lead 14 into a patient's vasculature system, fluid is introduced into the one or more hydraulic lumens formed in the outer surface 84 of the lead body 35. The introduction of fluid and thus, hydraulic pressure, into the hydraulic lumen or lumens causes the expandable fixation member or members to collapse from an expanded state to a collapsed state, such that they do not interfere with the lead's deployment. Hydraulic pressure is maintained in the hydraulic lumen(s) during insertion to prevent unwanted expansion of the fixation member prior to the distal end 42 of the lead 14 reaching its target destination within the heart 20. Leakage may occur within the hydraulic lumen and can be compensated for at the supply end by the introduction of additional fluid into the hydraulic lumen. The lead 14 is deployed through a patient's vasculature to a target location within the heart 20 using techniques known to those of skill in the art. Once the distal end 42 of the lead 14 has been positioned at the target location the fixation member or members can be deployed by releasing fluid from the hydraulic lumen or lumens. In the example where the lead body 35 includes more than one separately formed hydraulic lumen formed in the outer sheath, the fixation members may be selectively deployed as determined by one of skill in the art. The fixation member or members deploy with enough force to frictionally engage the wall of the vessel in which they are deployed thus providing for acute and even chronic fixation.

In the event that the distal end 42 of the lead needs to be repositioned, fluid may be re-introduced into the hydraulic lumens causing the fixation members to transition from an expanded state to a collapsed state. Once in the collapsed state, the distal end 42 of the lead 14 can be repositioned and the fixation member re-deployed by the release of hydraulic pressure from the hydraulic lumen. Alternatively, once the fixation members have been collapsed, the lead 14 can be retrieved from its location within a patient's heart 20.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described members. Accordingly, the scope of the present invention is intended to embrace all such alternatives, modifications, and variations as fall within the scope of the claims, together with all equivalents thereof.

We claim:

1. A medical electrical lead comprising:
   a lead body including a proximal portion and a distal portion and a primary lumen extending there between, the primary lumen adapted to receive a guiding member;
   at least one electrical conductor extending within the lead body;
   at least one electrode located on the lead body and operatively coupled to the at least one conductor;
   at least one hydraulic lumen having an inner wall formed in an outer sheath of the lead body, the at least one hydraulic lumen adapted to receive and contain a fluid;
   at least one plunger slideably disposed within the at least one hydraulic lumen adapted to receive and contain a fluid, wherein the plunger is moveable in a distal direction from a first position to a second position when hydraulic pressure is introduced into the lumen, the plunger comprising a plunger head in sealing contact with the inner wall of the at least one hydraulic lumen forming a circumferential seal facilitating hydraulic pressure build-up in the at least one hydraulic lumen; and
   at least one fixation portion along the lead body including at least one preformed fixation member having an expanded configuration and a collapsed configuration, the fixation member including a proximal end attached to an outer surface of the at least one fixation portion and a distal end attached to the plunger, wherein when the plunger is in the first position, the fixation member is in the expanded configuration.

2. The medical electrical lead according to claim 1, further comprising a slot located in an outer portion of the lead body, wherein the fixation member couples with the plunger through the slot.

3. The medical electrical lead according to claim 1, wherein the at least one fixation portion is located anywhere on the distal portion of the lead body.

4. The medical electrical lead according to claim 1, wherein the fixation portion is provided as a separate member adapted to be coupled to a distal end of the lead body.

5. The medical electrical lead according to claim 4, wherein the fixation portion comprises a hydraulic lumen in fluid communication with the at least one hydraulic lumen formed in the outer sheath of the medical electrical lead body and an inner lumen, the inner lumen in communication with the primary lumen of the medical electrical lead body, wherein the inner lumen is adapted to receive a guiding member.

6. The medical electrical lead according to claim 1, wherein the fixation member is a strut, tine, leg, loop, or stent-like structure.

7. The medical electrical lead according to claim 1, wherein when more than one fixation members are provided, the fixation members can be selectively deployed.

8. The medical electrical lead of claim 1, wherein the hydraulic lumen is an annular hydraulic lumen and the plunger is a cylindrical plunger.

9. The medical electrical lead of claim 1, wherein the fixation portion comprises two or more fixation members spaced an equal distance from one another on the lead body.

10. The medical electrical lead of claim 9, wherein the fixation members can be simultaneously actuated.

11. The medical electrical lead of claim 9, wherein the fixation members can be selectively activated.

12. A medical electrical lead comprising:
    a lead body, the lead body including an actuation lumen having an inner wall;
    at least one electrical conductor extending within the lead body;
    at least one electrode located on the lead body and operatively coupled to the at least one conductor;
    a plunger slideably disposed in the actuation lumen and moveable between a first position and a second position, the plunger in sealing contact with the inner wall forming a circumferential seal such that the actuation lumen is adapted to receive and contain a fluid; and
    a fixation member having a first end attached to the lead body and a second end attached to the plunger.

13. The medical electrical lead according to claim 12, further comprising a slot located in an outer portion of the lead body, wherein the fixation member couples with the plunger through the slot.

14. The medical electrical lead according to claim 12, wherein the fixation member can be located anywhere along a distal portion of the lead body.

15. The medical electrical lead according to claim 12, wherein the fixation member is a strut, tine, leg, loop, or stent-like structure.

16. The medical electrical lead according to claim 12, wherein the plunger is a cylindrical plunger.

17. A method of deploying a medical electrical lead to a location within a vessel:
    introducing fluid into a lumen having an inner wall formed within a lead body including at least one conductor extending therein and at least one electrode located on the lead body and operatively coupled to the at least one conductor;
    actuating at least one plunger slideably disposed in the lumen and in sealing contact with the inner wall of the lumen forming a circumferential seal facilitating pressure build-up in the at least one lumen;
    collapsing at least one fixation member located on a fixation portion of the lead body having a first end coupled to the lead body and a second end coupled to the plunger;
    guiding a distal end of the lead body through a patient's vasculature to a target location within the patient's heart;
    releasing fluid from the lumen; and
    expanding the fixation member to secure the distal end of the lead body at the target location.

18. The method according to claim 17, further comprising:
    re-introducing fluid into the lumen;
    re-collapsing the fixation member; and
    repositioning the distal end of the lead at the target location.

19. The method according to claim 17, further comprising:
    re-introducing fluid into the lumen;
    re-collapsing the fixation member; and
    removing the lead from the patient's heart.

20. A method of deploying a medical electrical lead including at least one conductor extending within a lead body and operatively coupled to at least one electrode located on the lead body to a location within a vessel, the method comprising introducing fluid into a lumen having an inner wall formed in a lead body and actuating a fixation member having a first end fixed to an outer surface of the lead body and a second end coupled to a plunger slideably disposed within the lumen and in sealing contact with the inner wall of the lumen forming a circumferential seal facilitating pressure build-up in the lumen.

* * * * *